(12) United States Patent
Daub et al.

(10) Patent No.: US 8,687,185 B2
(45) Date of Patent: Apr. 1, 2014

(54) DEVICE AND METHOD FOR OPTICAL PARALLEL ANALYSIS OF A SAMPLE ARRANGEMENT AND CORRESPONDING MANUFACTURING METHOD

(75) Inventors: Martina Daub, Weissach (DE); Jochen Rupp, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 376 days.

(21) Appl. No.: 13/023,078

(22) Filed: Feb. 8, 2011

(65) Prior Publication Data

US 2011/0194104 A1    Aug. 11, 2011

(30) Foreign Application Priority Data

Feb. 9, 2010   (DE) .......................... 10 2010 001 714

(51) Int. Cl.
*G01N 1/10* (2006.01)
*G01N 21/01* (2006.01)
*G01N 21/00* (2006.01)

(52) U.S. Cl.
USPC ........................... 356/246; 356/244; 356/432

(58) Field of Classification Search
USPC ................. 436/164; 422/82.05, 82.08, 82.09, 422/82.11, 435, 440
See application file for complete search history.

(56) References Cited

U.S. PATENT DOCUMENTS

| | | | | |
|---|---|---|---|---|
| 4,431,924 | A * | 2/1984 | Suovaniemi et al. | 250/566 |
| 5,506,676 | A * | 4/1996 | Hendler et al. | 356/237.1 |
| 6,887,701 | B2 * | 5/2005 | Anderson et al. | 435/287.1 |
| 2003/0142309 | A1 * | 7/2003 | Kuebler et al. | 356/338 |
| 2004/0142365 | A1 * | 7/2004 | Bao et al. | 435/6 |
| 2004/0159798 | A1 * | 8/2004 | Martin et al. | 250/458.1 |
| 2010/0141951 | A1 * | 6/2010 | Ali et al. | 356/436 |
| 2010/0321696 | A1 * | 12/2010 | Malik et al. | 356/432 |
| 2012/0154791 | A1 * | 6/2012 | Kuo et al. | 356/51 |

FOREIGN PATENT DOCUMENTS

DE    197 48 211    5/1999

* cited by examiner

*Primary Examiner* — Gregory J Toatley
*Assistant Examiner* — Hina F Ayub
(74) *Attorney, Agent, or Firm* — Kenyon & Kenyon LLP

(57) ABSTRACT

A device and a method for optical parallel analysis of a sample arrangement. The device includes a system of sample areas provided on and/or in a front face of the carrier substrate for receiving a sample substance; a system of detector areas provided on and/or in a back face of the carrier substrate, each detector area being assigned to a corresponding sample area; and a system of optical devices, each optical system being assigned to a corresponding sample area and being designed in such a way that it deflects light beams, which the corresponding sample area in response to an optical excitation does not emit in the direction of a detector area assigned to it, in the direction of the detector area assigned to it and/or in the direction of a detector-free area on the back face of the carrier substrate.

19 Claims, 4 Drawing Sheets

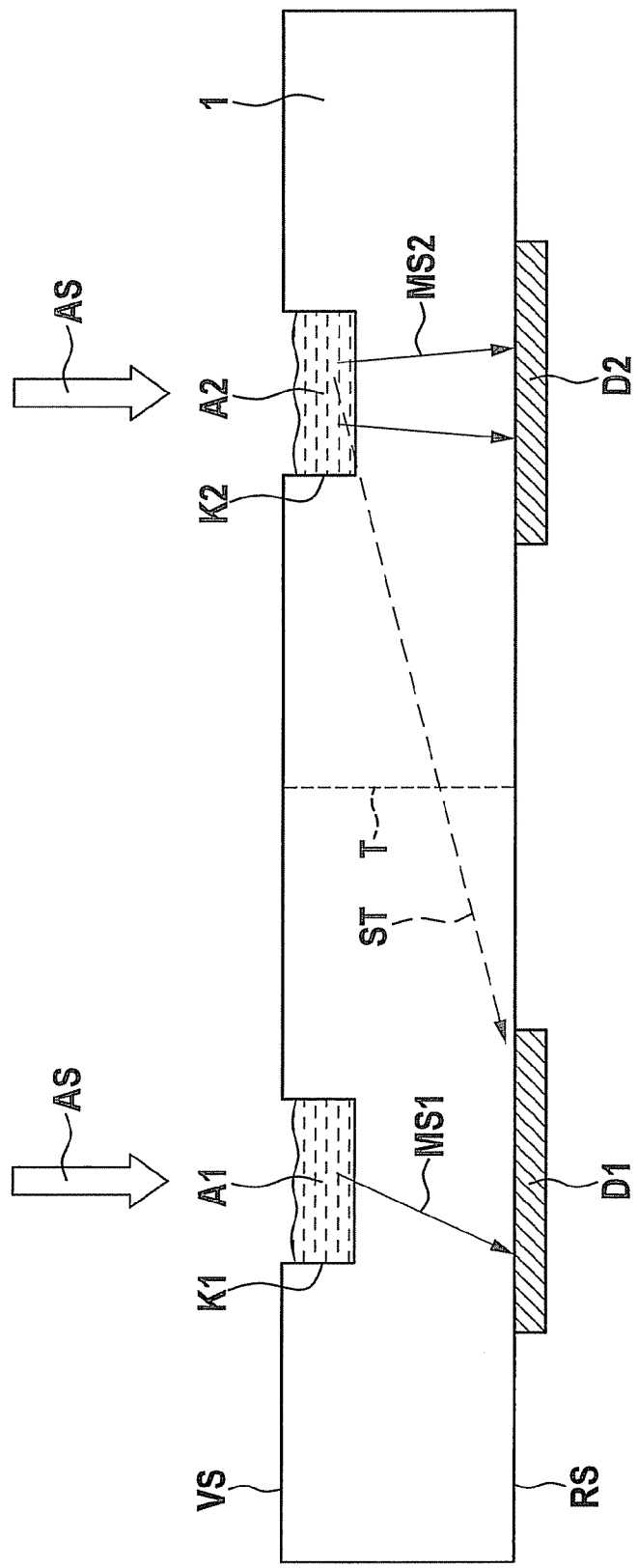

DEVICE AND METHOD FOR OPTICAL PARALLEL ANALYSIS OF A SAMPLE ARRANGEMENT AND CORRESPONDING MANUFACTURING METHOD

RELATED APPLICATION INFORMATION

The present application claims priority to and the benefit of German patent application no. 10 2010 001 714.0, which was filed in Germany on Feb. 9, 2010, the disclosure of which is incorporated herein by reference.

FIELD OF THE INVENTION

The present invention relates to a device and a method for optical parallel analysis of a sample arrangement, and to a corresponding manufacturing method.

BACKGROUND INFORMATION

Although applicable to any devices for optical parallel analysis of a sample arrangement, the exemplary embodiments and/or exemplary methods of the present invention and the problem on which it is based are explained with regard to utilization in microtiter plates.

For optical analyses of individual biochemical samples, microtiter plates or DNA chips are frequently used, on which the objects of analysis are provided, spatially separated from each other in discrete sample areas. Faster results are achieved through parallel performance of the optical analysis on a large number of individual samples than with sequential performance of individual analyses. Moreover, miniaturization of the individual batches results in a saving of reagent.

Microtiter plates are usually rectangular, and contain as sample areas many mutually isolated miniature cups in rows and columns for testing biological properties and reactions, for example through measurements of absorption, fluorescence and luminescence, for example for so-called high-throughput screening (HTS), in pharmaceutical and plant protection research. In most cases the plates are made of plastic, normally polystyrols, sometimes also polyvinyl chloride, but for very special applications also glass. The exact dimensions, according to the ANSI standard, are 127.76 mm×85.48 mm×14.35 mm. There are a multitude of formats, all on the same base area and in some cases having variable height, there normally being between 6 and 1536 miniature cups present. The miniature cups are available in various shapes, for example as flat bottoms, as flat bottoms with minimally rounded corners, as conically tapering bottoms, as U-shaped depressions.

Because of the small sample quantity required and the possibility of automation, microtiter plates have gained acceptance as an important element for research in the areas of pharmaceutics, medicine, biochemistry, genetics and molecular biology.

An optical system having a lens array and a field lens which depicts an object array on a detector array is discussed in DE 197 48 211 A1.

A device is discussed in DE 100 17 824 A1 for parallel photometric fluorescence or luminescence analysis of a plurality of mutually separated sample areas on an object.

FIG. 4 is a schematic depiction of a known device for optical parallel analysis of a sample arrangement in the form of a microtiter plate.

In FIG. 4, reference numeral 1 designates a carrier substrate 1 of plastic in the form of a microtiter plate. In front face VS of carrier substrate 1 an arrangement of sample areas K1, K2 is provided for receiving a sample substance A1, A2. Sample areas K1, K2 are cavities which have been formed, bored or milled into carrier substrate 1.

Placed on back face RS of carrier substrate 1 are detector areas D1, D2, which are each assigned to a corresponding sample area K1, K2. Thus each sample area K1, K2 with the associated detector area D1, D2 takes up essentially the same space, which is indicated by a virtual dividing line T.

If the sample substances are irradiated from front face VS of carrier plate 1 with excitation radiation AS in the course of an optical parallel analysis, then emissions occur in sample substance A1, A2, which involve beams MS1, MS2 and ST, for example light beams. Beams MS1 and MS2 are directed at detector areas D1 and D2, which are assigned to sample areas K1 and K2, with sample substance A1 and A2. These beams MS1, MS2 are thus regular measuring signals.

Light beam ST passes from sample substance A2 to detector area D1, which is assigned to sample area K1 with sample substance A1. In this respect, light beam ST is an interfering beam and lowers the signal-to-noise ratio of sample area K1. In other words, beam ST forms an optical contamination of the measuring signal of detector area D1, since it is stray light from adjacent sample area K2.

SUMMARY OF THE INVENTION

The device according to the present invention defined herein for optical parallel analysis of a sample arrangement, and the corresponding method according to the description herein, as well as the corresponding manufacturing method according to the description herein, have the advantage that they increase the sensitivity of the optical parallel analysis, so that they make a higher signal-to-noise ratio possible.

The idea underlying the exemplary embodiments and/or exemplary methods of the present invention consists in preventing optical contamination of the measuring signal by stray light from adjacent sample areas, and furthermore the optical signal may be bundled itself.

This is done through the use of a particular optical device which is assigned to a corresponding sample area, and is designed in such a way that it deflects the light beams, which the corresponding sample area in response to an optical excitation does not emit in the direction of a detector area assigned to it, in the direction of the detector area assigned to it and/or in the direction of a detector-free area on the back face of the carrier substrate. In particular, horizontally emitted light is easily deflected and focused onto the bottom of the carrier substrate, for example a microtiter plate, into the assigned detector area.

Thus, in addition to extension or avoidance of cross-sensitivity due to stray light from adjacent sample areas, it is possible to achieve an increase in the sensitivity of the optical signal by intensity increase or focusing.

At the same time, the necessary optical and geometric properties, such as transparency and flat construction of the carrier substrate, are not negatively impaired by the modification according to the present invention. Thus the behavior of the carrier substrate during use does not change, and it does not require modification of the known measuring methods.

The features listed and described herein relate to advantageous refinements and improvements of the particular object of the invention.

According to a refinement, the optical devices have totally reflective angular surfaces. This specific embodiment is particularly easy to manufacture.

According to another refinement, the optical devices have mirrored angular surfaces. In this specific embodiment the deflection angle is freely definable.

According to another refinement, the optical devices have mirrored spherical sector surfaces. This specific embodiment enables particularly good focusing on the particular detector area.

Exemplary embodiments of the present invention are illustrated in the drawing and explained in greater detail in the following description.

BRIEF DESCRIPTION OF THE DRAWINGS

FIG. 4 shows a schematic depiction of a known device for optical parallel analysis of a sample arrangement in the form of a microtiter plate.

DETAILED DESCRIPTION

Figure 1:
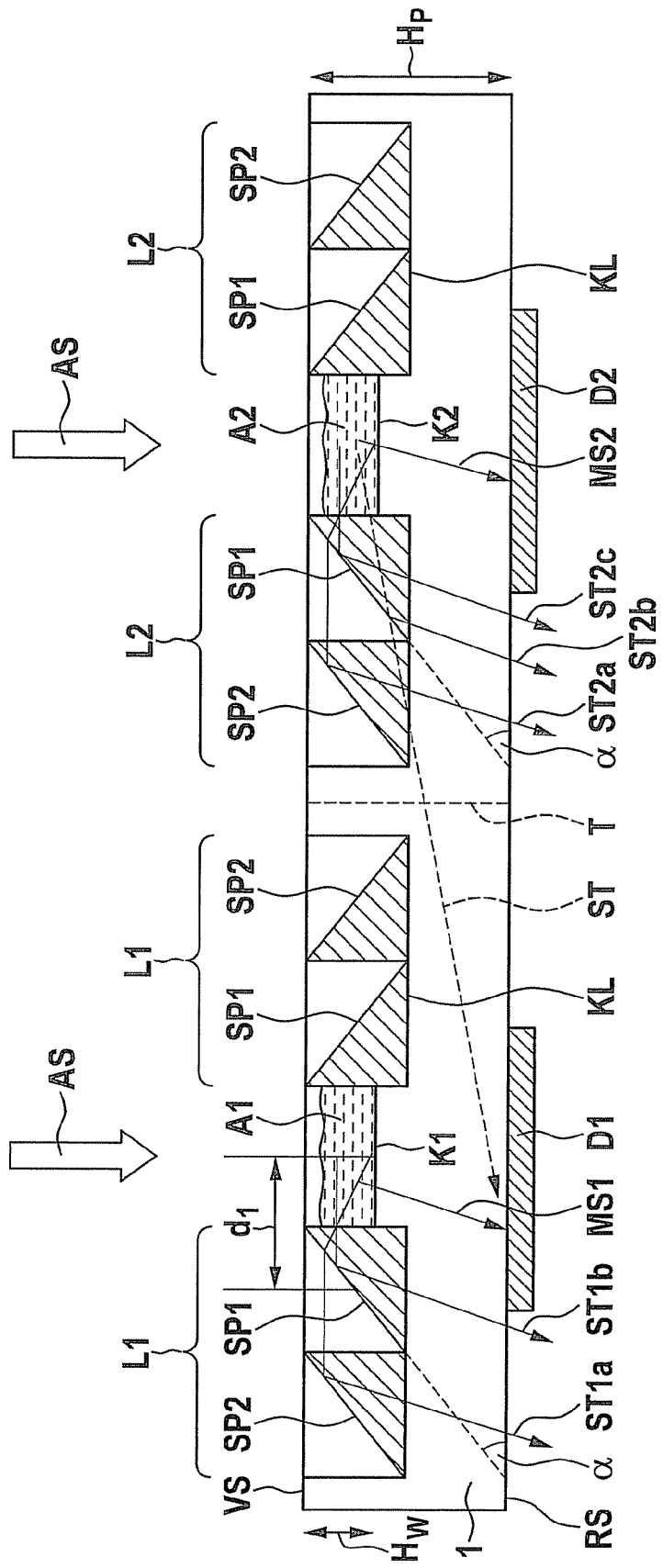
FIG. 1 shows a schematic depiction of a device for optical parallel analysis of a sample arrangement in the form of a microtiter plate according to a first specific embodiment of the present invention.

In the figures, the same reference numerals designate the same or functionally equivalent elements.

FIG. 1 is a schematic depiction of a device for optical parallel analysis of a sample arrangement in the form of a microtiter plate according to a first specific embodiment of the present invention.

In FIG. 1, reference numeral 1 designates a carrier substrate made of plastic in the form of a microtiter plate. Like the microtiter plate explained in reference to FIG. 4, carrier substrate 1 has cavities K1, K2 as sample areas for receiving a sample substance A1, A2. Sample areas K1, K2 etc. are normally arranged in matrix form on a rectangular carrier substrate 1. Carrier substrate 1 has a thickness $H_P$ of between 2 mm and 4 mm. The depth of sample areas K1, K2 is designated by $H_W$, and is usually 0.6 mm-0.8 mm.

Reference numerals L1, L2 each designate an optical device which is situated around sample area K1 and K2, namely ring-shaped in the present example, and which is designed in such a way that it deflects light beams ST1a, ST1b or ST2a, ST2b, ST2c, which the corresponding sample area K1, K2 in response to optical excitation radiation AS does not emit in the direction of the particular assigned detector area D1 and D2, in the direction of a detector-free area on back face RS of carrier substrate 1.

This is done in the present case through deflection on totally reflective angular surfaces SP1, SP2, which are situated in concentric rings around the respective sample area K1, K2. The total reflection is based on the optical properties of the material of carrier substrate 1 and of the environment (for example air). During total reflection, the light below a critical angle is reflected. For producing angular surfaces SP1, SP2, which are likewise situated in a cavity KL below front face VS, requires no additional plant expense and no additional production step, since such microtiter plates are made of plastic in most cases and obtain their shape with the aid of deep drawing processes or injection molding processes or stamping processes. Due to the use of optical devices L1, L2 interfering beams ST cannot occur, as explained earlier in reference to FIG. 4. Thus only measuring beams MS1 or MS2, which originate from the associated sample area and the sample substance A1 and A2 contained therein, reach detector areas D1, D2.

The condition for total reflection, which must be fulfilled, is:

$$\Theta = \arcsin\left(\frac{n_{air}}{n_1}\right)$$

where $n_{air}$ is the refractive index of air and $n_1$ is the refractive index of plastic. Typical values in the plastics used are $n_1=1.5$ (PC, COC) and $n_{air}=\sim 1$, which results in an angle of $\alpha<40°$ for total reflection with standard commercially available microtiter plate thicknesses as described above.

Figure 2:
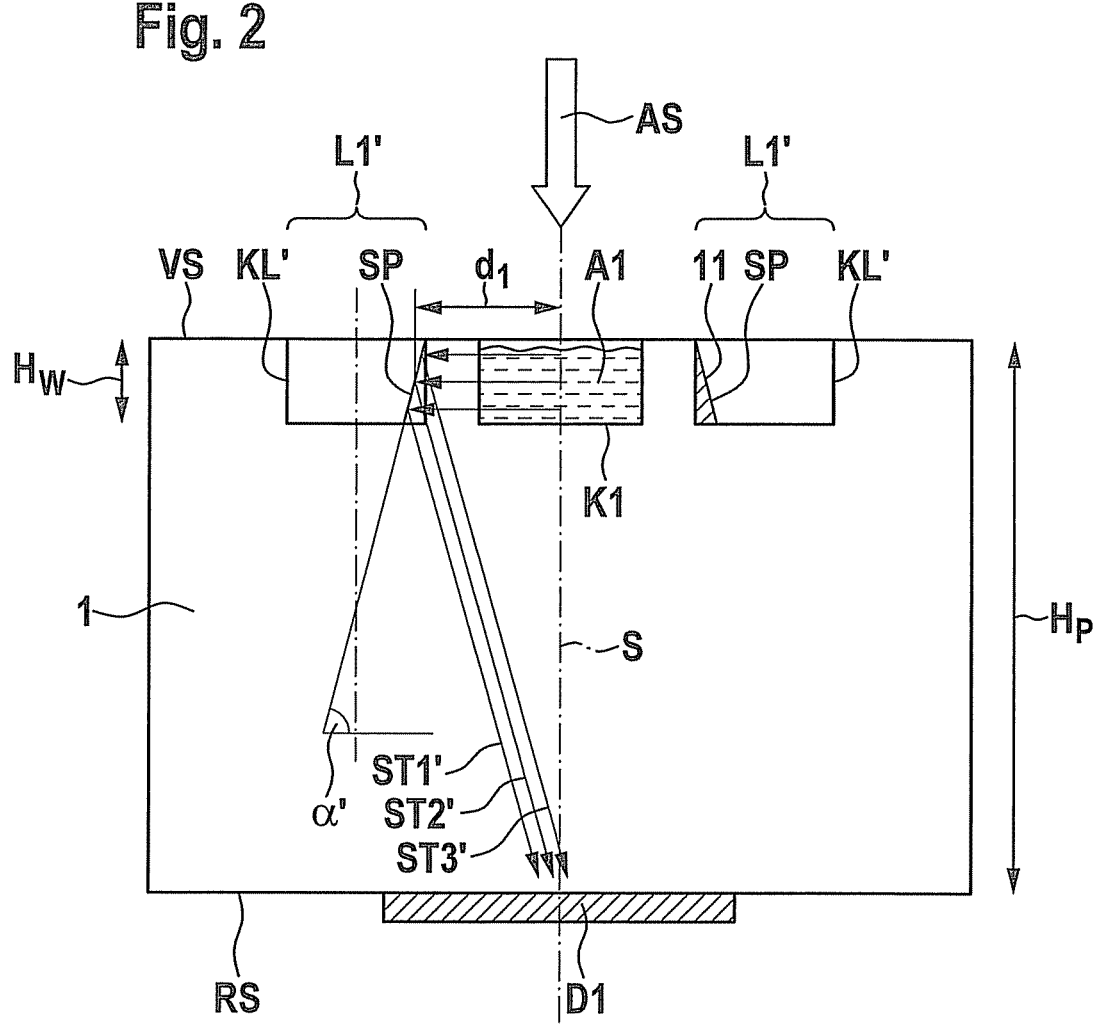
FIG. 2 shows a schematic depiction of a device for optical parallel analysis of a sample arrangement in the form of a microtiter plate according to a second specific embodiment of the present invention.

FIG. 2 is a schematic depiction of a device for optical parallel analysis of a sample arrangement in the form of a microtiter plate according to a second specific embodiment of the present invention.

In the specific embodiment according to FIG. 2, an optical device L1' is provided around sample area K1 including sample substance A1, which has a mirrored angular surface SP in a cavity KL' and which focuses beams ST1', ST2', ST3' that are not directed at detector area D1 on the latter, so that the measuring signal intensity is increased and the interfering signal intensity of other detector areas is reduced.

Mirrored angular surface SP is also attainable using the usual manufacturing process, as explained earlier in reference to FIG. 1, and the mirror finish with the aid of a metal layer M, for example gold, is achievable for example by vapor-depositing under a mask.

A particular advantage of this specific embodiment is the free choice of mirror angle $\alpha'$, whereby a focusing of beams ST1', ST2', ST3' on the associated detector area D1 is achievable. In that way, the additional process expense for the mirror finish, for example by sputtering, vapor-depositing or foil stamping, is more than compensated for by improved functionality.

Depending on the microtiter plate thickness $H_W$, the condition $$\alpha = \frac{1}{2}\arctan\left(\frac{H_W}{d_1}\right)$$

must be fulfilled. Here $d_1$ is the distance from center intersection line S of sample area K1 to the center of the mirrored angular surface SP, as indicated in FIG. 2.

Figure 3:
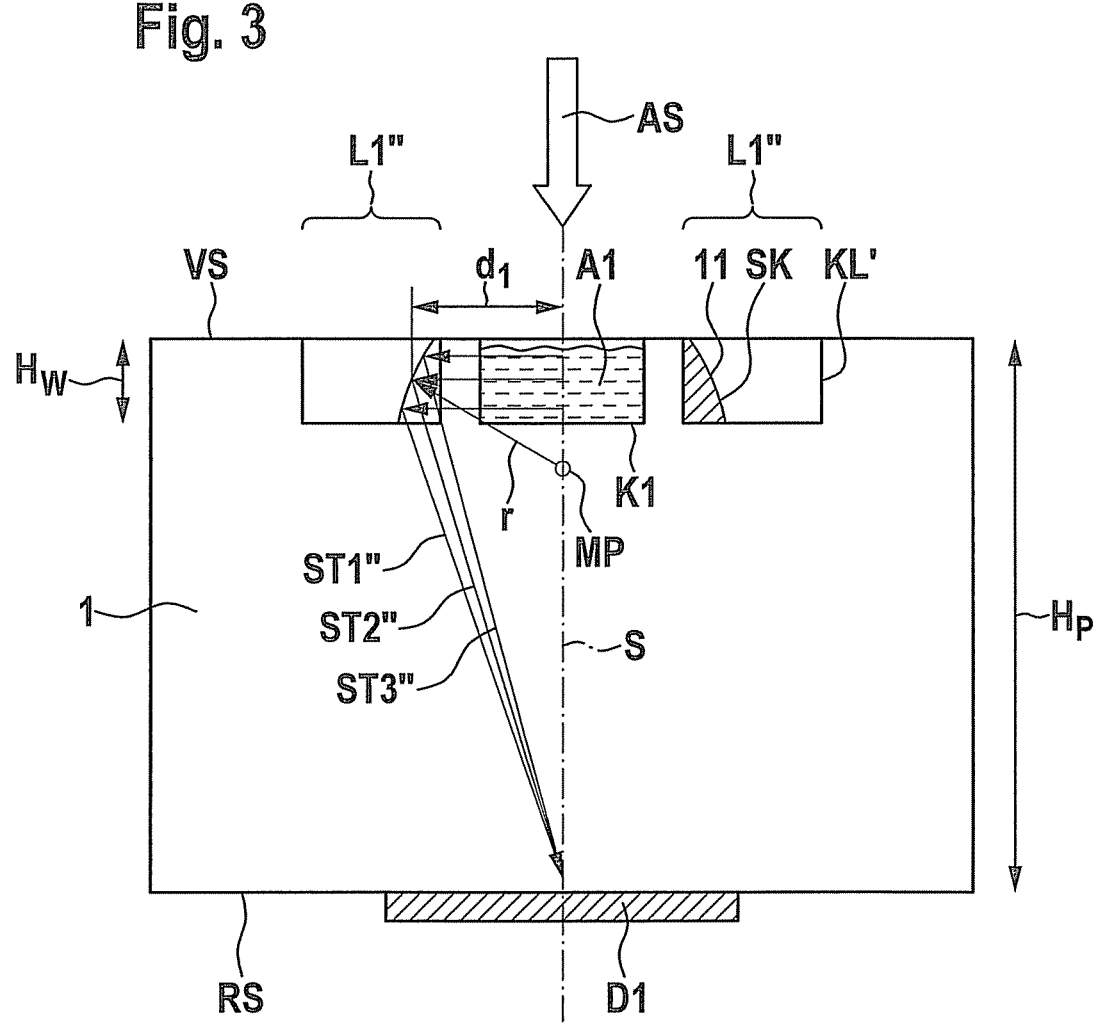
FIG. 3 shows a schematic depiction of a device for optical parallel analysis of a sample arrangement in the form of a microtiter plate according to a third specific embodiment of the present invention.

FIG. 3 is a schematic depiction of a device for optical parallel analysis of a sample arrangement in the form of a microtiter plate according to a third specific embodiment of the present invention.

In the third specific embodiment according to FIG. 3, in contrast to the second specific embodiment according to FIG. 2, a spherical sector surface SK is provided with a mirror layer M, for example of gold. The center point of the associated sphere is designated schematically with reference symbol MP, the radius with reference symbol r.

This has the particular advantage that beams ST1", ST2", ST3", which are originally not directed at the assigned detector area D1, may be focused even better.

Although the exemplary embodiments and/or exemplary methods of the present invention has been described above on the basis of exemplary embodiments, it is not limited to these but is modifiable in many ways.

Although the exemplary embodiments and/or exemplary methods of the present invention have been described in connection with microtiter plates, it is not limited thereto but is applicable in principle to all carrier substrates for optical parallel analysis. The optical devices also do not have to be integrated into the carrier substrate, but may be provided on its surface as discrete elements.

The detector areas may either be fixed on the back face of the carrier substrate, as shown in the above exemplary embodiments, or may also be provided in the interior of the carrier substrate, or may be located at a distance from the carrier substrate.

What is claimed is:

1. A device for providing optical parallel analysis of a sample arrangement, comprising:
    a carrier substrate;
    a system of sample areas provided on and/or in a front face of the carrier substrate, for receiving a sample substance;
    a system of detector areas provided on and/or in a back face of the carrier substrate, wherein one detector area is assigned to each corresponding sample area; and
    a system of optical devices, each optical device being assigned to a corresponding sample area and being configured so that it deflects light beams, which the corresponding sample area in response to an optical excitation does not emit in the direction of a detector area assigned to it, in the direction of the detector area assigned to it and/or in the direction of a detector-free area on the back face of the carrier substrate wherein at least one of the optical devices focuses the light beams onto the detector area assigned to it and/or in the direction of the detector-free area on the back face of the carrier substrate.

2. The device of claim 1, wherein the sample areas include first cavities in the front face of the carrier substrate.

3. The device of claim 2, wherein the optical devices are provided in second cavities in the front face of the carrier substrate, which surround the first cavities.

4. The device of claim 3, wherein the optical devices have totally reflective angular surfaces.

5. The device of claim 3, wherein the optical devices have mirrored angular surfaces.

6. The device of claim 3, wherein the optical devices have mirrored spherical sector surfaces.

7. The device of claim 3, wherein the second cavities with the optical devices surround the sample areas in a ring shape, in particular circularly.

8. The device of claim 1, wherein the carrier substrate is a microtiter plate.

9. The device of claim 1, wherein the optical devices are integrated into the carrier substrate.

10. A method for providing optical parallel analysis of a sample arrangement, the method comprising:
    providing a device providing optical parallel analysis of a sample arrangement, the device including:
        a carrier substrate;
        a system of sample areas provided on and/or in a front face of the carrier substrate, for receiving a sample substance;
        a system of detector areas provided on and/or in a back face of the carrier substrate, wherein one detector area is assigned to each corresponding sample area; and
        a system of optical devices, each optical device being assigned to a corresponding sample area and being configured so that it deflects light beams, which the corresponding sample area in response to an optical excitation does not emit in the direction of a detector area assigned to it, in the direction of the detector area assigned to it and/or in the direction of a detector-free area on the back face of the carrier substrate wherein at least one of the optical devices focuses the light beams onto the detector area assigned to it and/or in the direction of the detector-free area on the back face of the carrier substrate;
    providing parallel optical excitation of the sample arrangement by irradiating the front face of the carrier substrate; and
    detecting the optical response of the sample areas in their particular detector area.

11. A method for manufacturing a device for providing optical parallel analysis of a sample arrangement, the method comprising:
    providing a carrier substrate;
    providing a system of sample areas provided on and/or in a front face of the carrier substrate, for receiving a sample substance;
    providing a system of detector areas on and/or in a back face of the carrier substrate, wherein one detector area is assigned to each corresponding sample area; and
    providing a system of optical devices, each optical system being assigned to a corresponding sample area and being configured so that it deflects light beams, which the corresponding sample area in response to an optical excitation does not emit in the direction of a detector area assigned to it, in the direction of the detector area assigned to it and/or in the direction of a detector-free area on the back face of the carrier substrate wherein at least one of the optical devices focuses the light beams onto the detector area assigned to it and/or in the direction of the detector-free area on the back face of the carrier substrate;
    wherein the optical devices are integrated into the carrier substrate by one of a deep drawing process, an injection molding process, and a stamping process.

12. The device of claim 1, wherein each optical system device includes at least one surface arranged at an angle to the detector area assigned to it.

13. The device of claim 12, wherein the angle is not 90°.

14. The device of claim 10, wherein each optical device includes at least one surface arranged at an angle to the detector area assigned to it.

15. The device of claim 14, wherein the angle is not 90°.

16. The device of claim 11, wherein each optical device includes at least one surface arranged at an angle to the detector area assigned to it.

17. The device of claim 16, wherein the angle is not 90°.

18. The device of claim 5, wherein at least one of the mirrored angular surfaces is finished with the aid of a metal layer, wherein the mirror finish is achieved by sputtering, vapor-depositing, or foil stamping.

19. The device of claim 18, wherein the metal layer includes gold.

* * * * *